United States Patent [19]

Murashita et al.

[11] Patent Number: 5,568,812
[45] Date of Patent: Oct. 29, 1996

[54] DIAGNOSTIC ULTRASOUND APPARATUS

[75] Inventors: Masaru Murashita; Hiroyuki Kawada; Toshiyuki Matsunaka, all of Mitaka, Japan

[73] Assignee: Aloka Co., Ltd., Japan

[21] Appl. No.: 377,327

[22] Filed: Jan. 24, 1995

[30] Foreign Application Priority Data

Jan. 25, 1994 [JP] Japan ................................. 6-006624

[51] Int. Cl.$^6$ .................................................. A61B 8/00
[52] U.S. Cl. ............................ 128/660.04; 128/661.04
[58] Field of Search ................... 128/660.04–660.05, 128/661.04, 661.07–661.1; 73/861.25

[56] References Cited

U.S. PATENT DOCUMENTS

| | | | |
|---|---|---|---|
| 4,501,277 | 2/1985 | Hongo | 128/661.04 X |
| 4,817,619 | 4/1989 | Sugiyama et al. | 128/661.09 |
| 4,972,838 | 11/1990 | Yamazaki | 128/660.05 X |
| 5,425,365 | 6/1995 | Iinuma | 128/660.05 |

*Primary Examiner*—Francis Jaworski
*Attorney, Agent, or Firm*—Marger, Johnson, McCollom & Stolowitz, P.C.

[57] ABSTRACT

A diagnostic ultrasound apparatus includes an ultrasound probe for transmitting and receiving ultrasound beams to and from an object to be observed; a frame memory for storing B-mode ultrasound image data of the object obtained from the ultrasound beams received by the ultrasound probe; a monitor for displaying at least a B-mode ultrasound image of the object formed on the basis of the B-mode ultrasound image data stored in the frame memory; a sampling line setting circuit for freely setting a desired course and range of at least one data sampling line for the B-mode image displayed on the monitor; and a read-out circuit for selectively reading out, from the ultrasound image data stored in the frame memory, ultrasound image data corresponding to the data sampling line. The ultrasound image data which has been read out by the read-out circuit is displayed on the monitor as an M-mode image. According to the diagnostic ultrasound apparatus, the data sampling line is established for any desired course and range unrelated to the forward direction of the ultrasound beams which form the B-mode image displayed on the monitor, and the ultrasound image data which corresponds to the data sampling line is selectively read out from the ultrasound image data of the B-mode image stored in the frame memory. The thus-obtained ultrasound image data of the data sampling line of the desired course, that is the M-mode image is displayed on the monitor. Therefore, observation and diagnosis of the state of motion of any specific part of the patient can be carried out freely in any direction irrespective of the forward direction of the ultrasound beams from the probe.

13 Claims, 8 Drawing Sheets

DIAGNOSTIC ULTRASOUND APPARATUS

BACKGROUND OF THE INVENTION

1. Field of the Invention

The present invention relates to a diagnostic ultrasound apparatus, and more particularly to a diagnostic ultrasound apparatus which can display changes of ultrasound image data with the lapse of time along a desired sampling line in a two-dimensional ultrasound image.

2. Description of the Prior Art

Generally, in the M-mode display of ultrasound diagnostic apparatuses, biological data (indicated by brightness and the like) of a living body taken along a specified ultrasound beam line (hereinafter referred to as the "M-mode scanning line") is plotted on the Y-axis and time is indicated by the X-axis, and this makes it possible to display biological changes, namely the state of motion, in the living body with the lapse of time on the M-mode scanning line.

Figure 1:
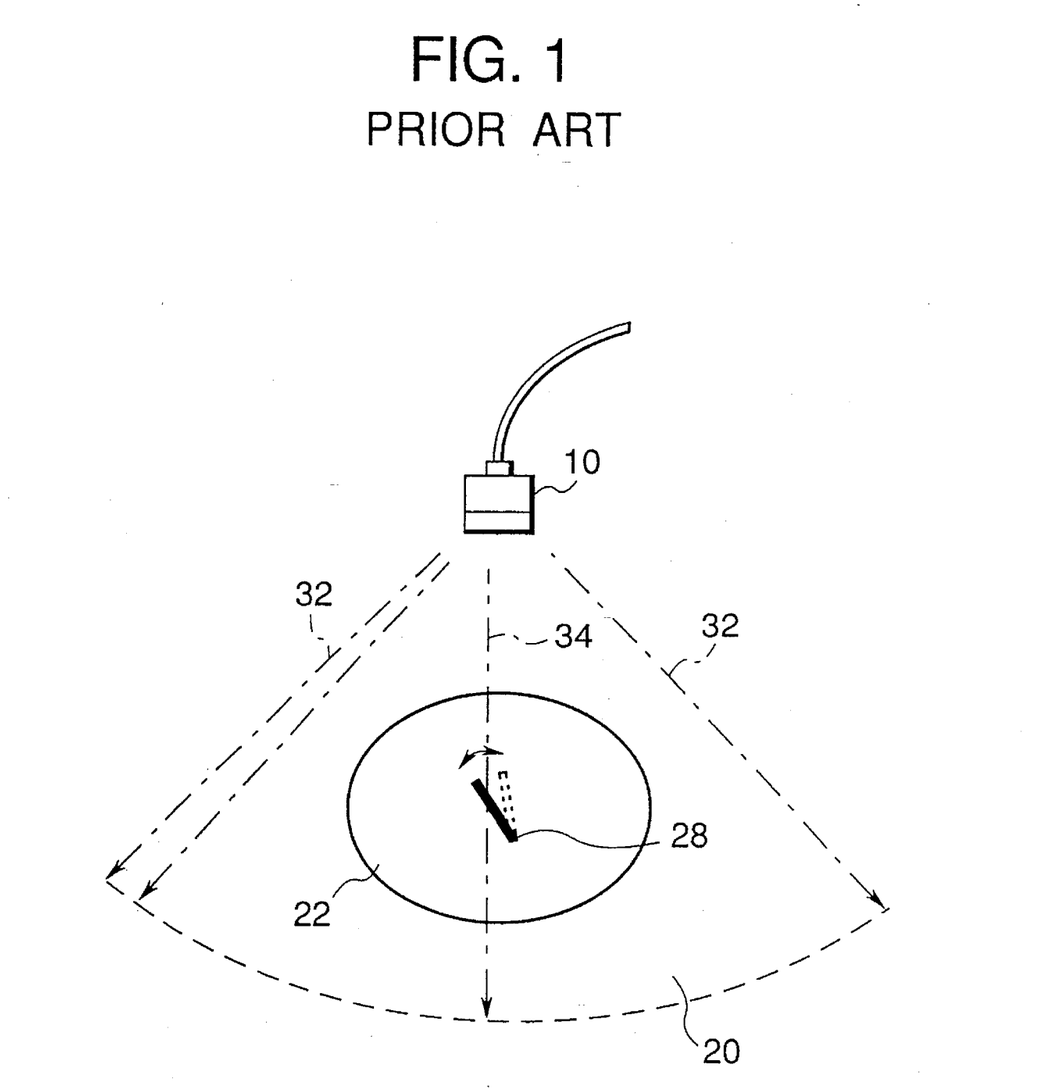
FIG. 1 is a conceptual drawing showing the relationship between a B-mode image and a data sampling line for an M-mode image according to the prior art.

In the prior art diagnostic ultrasound apparatus, the M-mode scanning line is obtained as shown in FIG. 1. Namely, an ultrasound probe 10 (hereinafter referred to as the "probe") carries out a B-mode scanning with respect to a diagnosed region in a patient such as a heart 22 thereof. The B-mode scanning includes a plurality of ultrasound beams 32 which are emitted from the probe 10 so as to form a sector shaped scanning area, for instance. On the basis of the echo data obtained by the B-mode scanning, a two-dimensional ultrasound scanning image, that is a B-mode image 20 as shown in FIG. 1 can be obtained. In this state, one ultrasound beam line 34 within the ultrasound beam lines which form the B-mode image is designated as an M-mode scanning line (sampling line). The state of motion of the heart with the lapse of time along the thus-obtained M-mode scanning line is indicated as the M-mode image on a display monitor of the diagnostic ultrasound apparatus.

Hereinafter, detailed descriptions are made with reference to the case where a mitral valve of a heart of a patient is observed by the M-mode scanning using the conventional diagnostic ultrasound apparatus. First, an operator confirms whether or not a mitral valve 28 of a heart 22 of the patient, which is to be observed, appears in the B-mode image 20 displayed on the monitor. Then, in the case where the mitral valve-28 is displayed, an M-mode scanning line 34 which passes through the mitral valve 28 is designated from ultrasound beam lines 32 which form the B-mode image 20.

Once an M-mode scanning line 34 is designated, transmission and reception of ultrasound waves are carried out only for this M-mode scanning line 34 by the probe 10, and biological data of the patient, that is the motion of the mitral valve 28 obtained along the M-mode scanning line 34 is displayed on the monitor. The changes in the patient along the M-mode scanning line 34 with the lapse of time becomes the M-mode image, and this M-mode image enables the operator to carry out observation/diagnosis of the state of motion of the mitral valve 28 of the heart 22 of the patient.

However, in such prior art M-mode displays, M-mode images can only be obtained along the M-mode scanning line 34 designated within the ultrasound beam lines which form a B-mode image. Moreover, in such an M-mode display, if the M-mode scanning line 34 is not substantially perpendicular to the portion being observed, that is in this example the mitral valve 28, it makes it impossible to obtain accurate observations of the state of motion of the mitral valve 28. As a result, the operator needs to estimate the position and motion of the mitral valve 28 and accordingly has to manually fix the position of the probe 10 itself in order to get the M-mode scanning line 34 to pass perpendicularly through the mitral valve 28. As a great deal of time is required in order to carry out such positioning of the probe 10, it is not possible to achieve the long-desired goal of shortening the time required for carrying out diagnosis.

Furthermore, since the object to be observed such as a heart is located within a body of a patient, it is surrounded by the rib bones of the patient. Therefore, when a diagnostic procedure is being carried out, for example when a diagnosis is being carried out on the cardiac function of a patient, the transmission and reception of ultrasound waves must be carried out through the space between the rib bones of the patient. This makes it very troublesome to arrange the probe 10 at an optimum position for viewing the specific portion of the heart to be observed such as a mitral valve. Accordingly, there is diminished reliability for such diagnosis.

SUMMARY OF THE INVENTION

The purpose of the present invention is to overcome the problems of the prior art mentioned above. Accordingly, it is an object of the present invention to provide a diagnostic ultrasound apparatus that is capable of carrying out observation/diagnosis of the state of motion of a portion of a living body to be observed along any desired direction or along any desired course that is unrelated to the forward directions of the ultrasound beams forming a B-mode image.

In order to achieve the above-stated object, the diagnostic ultrasound apparatus according to the present invention has the construction described below.

Namely, the diagnostic ultrasound apparatus according to the present invention comprises an ultrasound probe for transmitting and receiving ultrasound beams to and from an object to be observed; a frame memory for storing two-dimensional ultrasound image data of the object obtained from the ultrasound beams received by the ultrasound probe; a monitor for displaying at least a two-dimensional ultrasound image of the object formed on the basis of said two-dimensional ultrasound data stored in the frame memory; means for freely setting a desired course and range of at least one data sampling line for a two-dimensional ultrasound image displayed on the monitor; read-out means for selectively reading out, from the ultrasound image data stored in the frame memory, ultrasound image data corresponding to the data sampling line; and means for displaying an ultrasound image which corresponds to the data sampling line on the monitor on the basis of the ultrasound image data which has been read out by the read-out means.

In the diagnostic ultrasound apparatus according to the present invention, a data sampling line is established for any desired course and range unrelated to the forward direction of the ultrasound beams which form the B-mode image displayed on the monitor, and ultrasound image data which corresponds to the data sampling line is selectively read out from the ultrasound image data of the B-mode image stored in the frame memory. The thus-obtained ultrasound image data of the data sampling line of the desired course constitutes an M-mode image irrespective of the beam forwarding direction, and such M-mode image is displayed on the monitor. Therefore, observation and diagnosis of the state of motion of any specific part of a patient can be carried out freely in any desired direction without the probe having to be confined to a fixed position and without such observation/diagnosis being confined to the forward direction of the ultrasound beams from the probe.

Namely, according to the present invention, even if no ultrasound beams are transmitted perpendicular to the specific portion of the patient, it is possible to establish the data sampling line for the specific portion at any desired course on the B-mode image produced from the ultrasound beams. Therefore, it becomes easy to accurately observe and diagnose the state of motion of the specific portion with the M-mode image.

In this case, it is preferred that the diagnostic ultrasound apparatus according to the present invention also includes scanning control means for setting a scanning range within the two-dimensional ultrasound image on the basis of the data sampling line and for controlling the probe so as to perform scanning only within the scanning range. This means that scanning is carried out only within a specified ultrasound scanning range determined based on the designated data sampling line. Therefore, it is possible to improve frame rate for displaying the ultrasound image data for the data sampling line. Further, this makes it possible to carry out accurate observation and diagnosis of even rapidly moving portions of a living body.

Further, the present invention is also directed to a method of obtaining an M-mode image along any desired direction and range in a B-mode image displayed in a monitor. The method comprises the steps of: transmitting and receiving ultrasound beams to and from an object to be observed to obtain ultrasound image data which can produce the B-mode image; storing the ultrasound image data in a frame memory; designating any desired course of a data sampling line in the B-mode image displayed in the monitor irrespective of the ultrasound beams which form the B-mode image; and producing an M-mode image of the object along the desired data sampling line on the monitor on the basis of ultrasound image data corresponding to the data sampling line which is selectively obtained from the ultrasound image data of the B-mode image stored in the frame memory.

Other objects, structures and advantages of the present invention will be more apparent when the following detailed description of the preferred embodiments is taken into account in conjunction with the appended drawings.

DETAILED DESCRIPTION OF THE PREFERRED EMBODIMENTS

With reference to the appended drawings, a preferred embodiment of a diagnostic ultrasound apparatus according to the present invention will now be described below.

Figure 2:
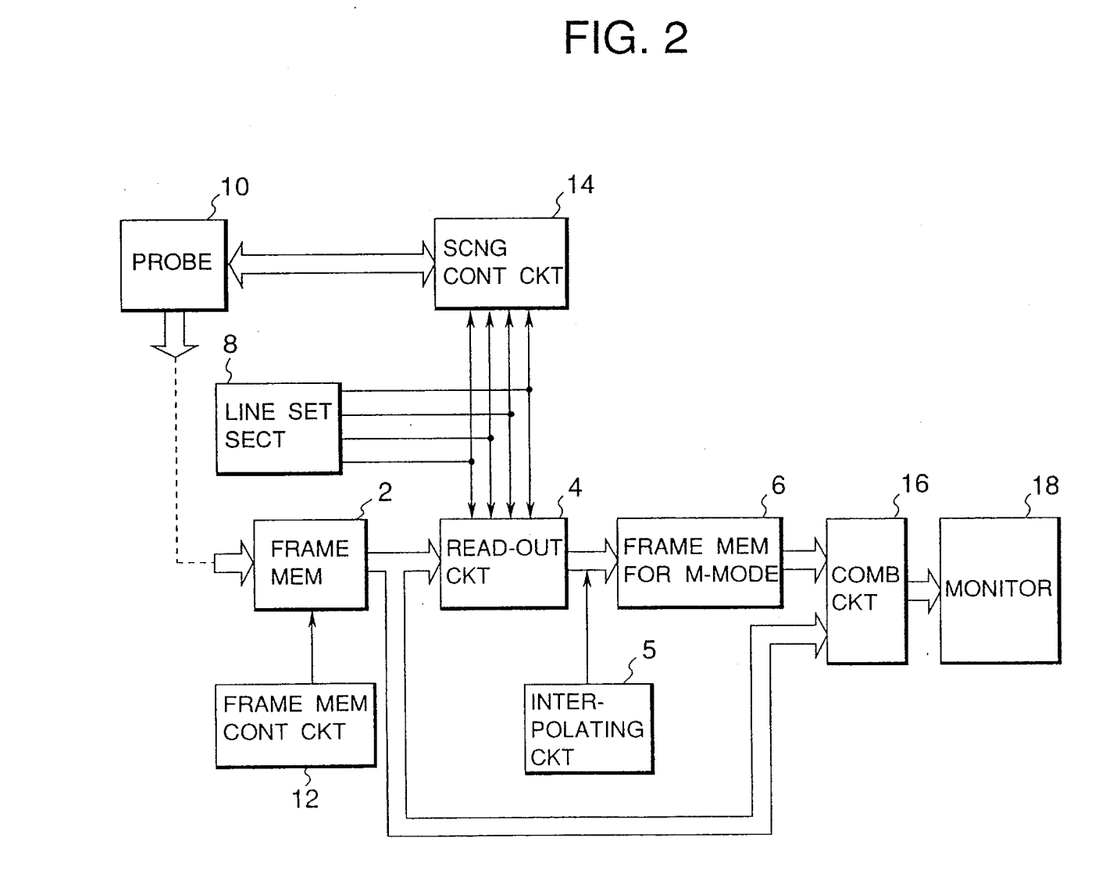
FIG. 2 is a block diagram showing the essential parts of a diagnostic ultrasound apparatus according to an embodiment of the present invention.

FIG. 2 is a block diagram of an embodiment of a diagnostic ultrasound apparatus according to the present invention.

As shown in FIG. 2, the diagnostic ultrasound apparatus includes a frame memory 2 which stores, frame by frame, the two-dimensional ultrasound image data of a patient obtained from a probe 10. The frame memory 2 is controlled by a frame memory control circuit 12.

A line setting section 8 is provided for enabling an operator to establish a data sampling line (described hereinbelow) for a two-dimensional ultrasound image displayed on a monitor 18. In practice, a mouse, a track ball, a keyboard or the like is used for this purpose.

Further, a scanning control circuit 14 is provided to decide the scanning range of the probe 10 based on the established data sampling line and to control the probe 10 so as to gather ultrasound image data from the scanning range.

A read-out circuit 4 is provided for selectively reading out, frame by frame, ultrasound image data corresponding to the data sampling line. An M-mode frame memory 6 is provided for sequentially storing the ultrasound image data outputted from the read-out circuit 4. In this regard, it should be noted that the read-out circuit 4 and the M-mode frame memory 6 are each controlled by a control circuit not shown in the drawings.

A combining circuit 16 is provided to combine the ultrasound image data corresponding to the data sampling line stored in the M-mode frame memory 6 and the two-dimensional ultrasound image data of the patient stored in the frame memory 2. In other words, the combining circuit 16 is provided to produce a composite image including a M-mode image formed from the ultrasound image data corresponding to the data sampling line which is stored in the M-mode frame memory 6 and a B-mode image formed from the ultrasound image data which is stored in the frame memory 2. As a result, the composite image including the M-mode image and the B-mode image can be displayed on the monitor 18.

Next, the operation of the diagnostic ultrasound apparatus according to the present embodiment will be described.

Figure 3:
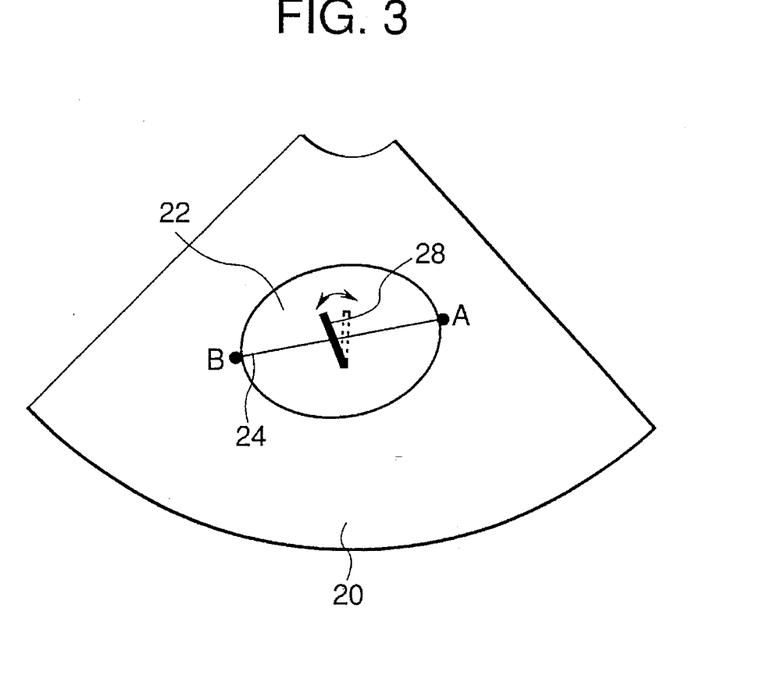
FIG. 3 illustrates an example display of a B-mode image according to the embodiment of the present invention.

First, ultrasound waves are transmitted from the probe 10 to an object to be observed in the patient and reflected ultrasound waves (echos) are received by the probe 10 to carry out a B-mode scanning with respect to the object. In this embodiment, it should be understood that the object to be observed is a mitral valve 28 inside a heart 22 of the patient. The received ultrasound waves are converted into digital signals and then stored in the frame memory 2 as B-mode ultrasound image data. The ultrasound image data is read-out from the frame memory 2 and then converted into analog signals. The analog signals are fed to the monitor 18 to produce a two-dimensional ultrasound image 20 (B-mode image), as shown in FIG. 3. In this regard, it should be noted that in this drawing the motion of the mitral valve 28 is indicated by the arrow.

Now, for the B-mode ultrasound image 20 displayed on the monitor 18, an operator operates the line setting section 8 to freely designate a desired data sampling line 24 in such a manner that it passes substantially perpendicular through the mitral valve 28. Here, as shown in FIG. 3, points A and B are designated and then the straight line that passes through these two points forms the data sampling line 24. In the case where more than two points are designated, the curved line that passes through such points will form the data sampling line 24.

Figure 4:
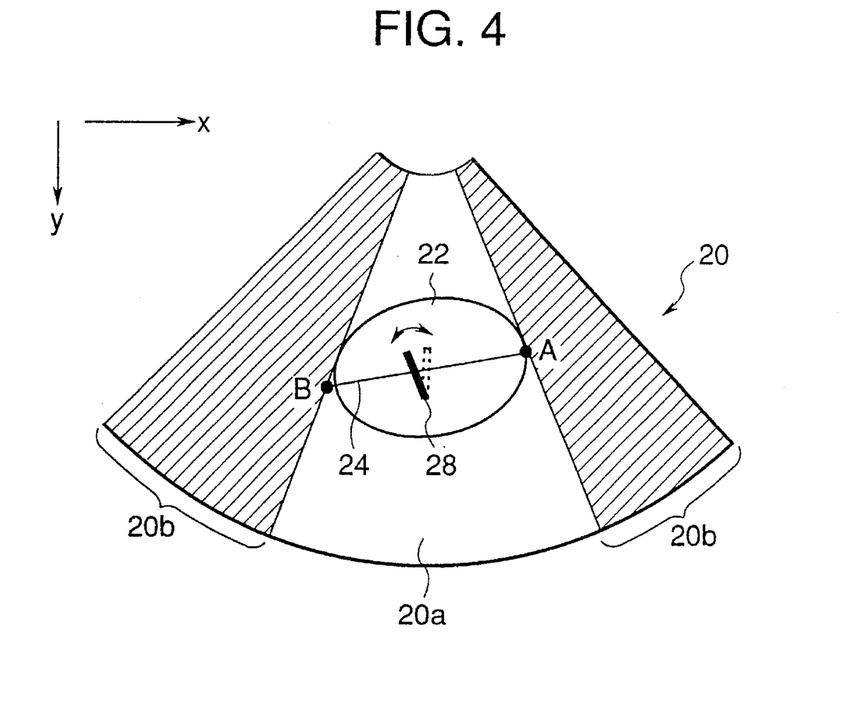
FIG. 4 illustrates an ultrasound scanning range after a data sampling line has been designated according to the embodiment of the present invention.

On the data sampling line 24 has been designated, the scanning control circuit 14 determines the minimum ultrasound scanning range 20a (hereinafter, referred to as 'M-mode scanning range') necessary for the ultrasound image 20 shown in FIG. 4 based on the X and Y coordinates of the designated points A and B and the data sampling line 24. In this case, the smallest and largest X and Y values of the designated data sampling line 24 with respect to X and Y coordinates are defined by points A and B, so that the M-mode scanning range 20a is determined so as to lie between points A and B. This means that the scanning angle is determined by points A and B. In addition, as the need arises, it is also possible to set an appropriate depth of the scanning on the basis of the smallest X and Y values.

As a result of such determination, the scanning control circuit 14 co. Nitro the probe 10 so that it carries out transmission and reception of ultrasound waves only within the M-mode scanning range 20a. Namely, no transmission and reception of ultrasound waves is carried out for the regions 20b that lie outside and are unrelated to the ultrasound image data along the data sampling line 24. This serves to improve frame rate for displaying the M-mode image as explained later.

Next, the ultrasound image data obtained from the ultrasound scanning range 20a is stored sequentially in the frame memory 2 and is then sequentially outputted from the frame memory 2. In this case, the read-out circuit 4 selectively reads out, frame by frame, the ultrasound image data corresponding to the data sampling line 24 from the ultrasound image data outputted from the frame memory 2, and then this data is outputted to the M-mode frame memory 6.

The M-mode frame memory 6 sequentially stores the ultrasound image data, that is 'M-mode image data' which has been selectively read out, and then this data is outputted to the combining circuit 16.

Figure 5:
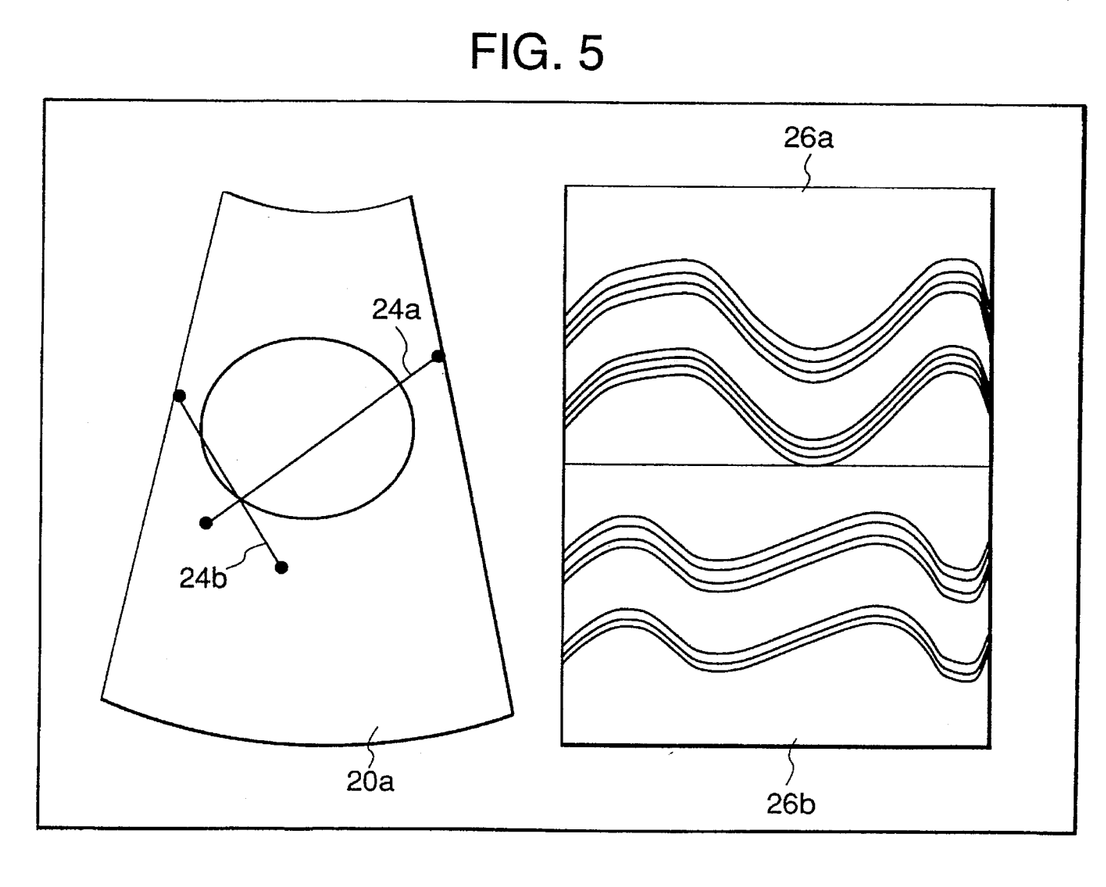
FIG. 5 shows an example of a composite image including a B-mode image and an M-mode image obtained along the data sampling line according to the embodiment of the present invention.

After the M-mode image data has been outputted from the M-mode frame memory 6, the combining circuit 16 combines this M-mode image data and the B-mode image data outputted from the frame memory 2 so as to produce a composite image including a B-mode image and an M-mode image, and this combined data is then outputted to the monitor 18. Then, as shown in FIG. 5, the composite image including the B-mode image 20a and the M-mode image (262a, 26b) is displayed on the monitor 18. However, both the B-mode and M-mode images do not necessarily need to be displayed at the same time, and it is also possible to display only the M-mode image on the monitor 18.

With the above-described structure of the present embodiment, it is possible to obtain M-mode images along any freely chosen direction or course for portions of a patient that previously could only be observed along the ultrasound beam line.

Furthermore, as shown in FIG. 5, if a plural number of data sampling lines 24a, 24b are designated for a single B-mode image 20a, it is possible to obtain respective M-mode images 26a, 26b corresponding to such data sampling lines 24a, 24b. In this way, it is possible to obtain M-mode image data of two different portions at the same time, thereby making it possible to carry out observation and diagnosis from various observation points. Also, as described above, the data sampling line 24 need not be limited to a straight line, but instead may be designated as a curved line.

Moreover, in the present embodiment, once the ultrasound scanning range 20a has been determined based on designated points A and B and the data sampling line 24, as was described above, transmission and reception of ultrasound waves are carried out only for the ultrasound scanning range 20a. This makes it possible to minimize the time required for obtaining ultrasound image data for a single frame. Accordingly, it becomes possible to improve the frame rate for displaying the ultrasound image, and this makes it possible to carry out accurate observations of the state of motion even for rapidly moving portions within a living body.

Hereinafter, an explanation will be given for the way in which the ultrasound image data is made to correspond with the data sampling line according to the present embodiment.

Figure 6:
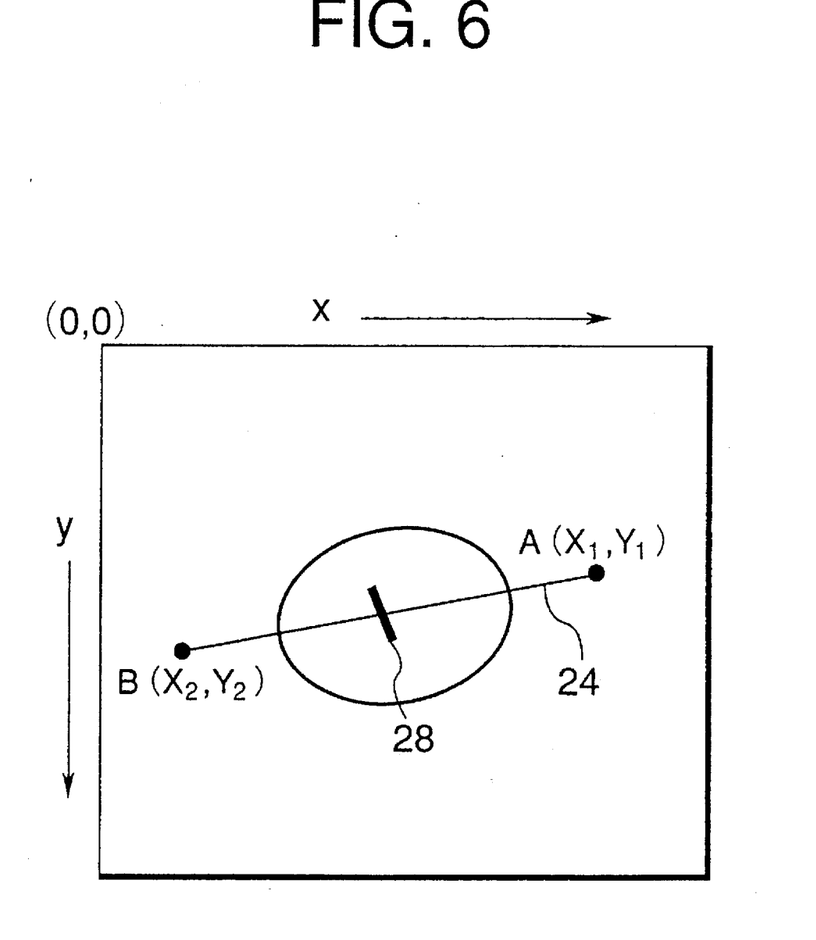
FIG. 6 is a conceptual drawing used for explaining the way in which a data sampling line is designated according to the embodiment of the present invention.
Figure 7:
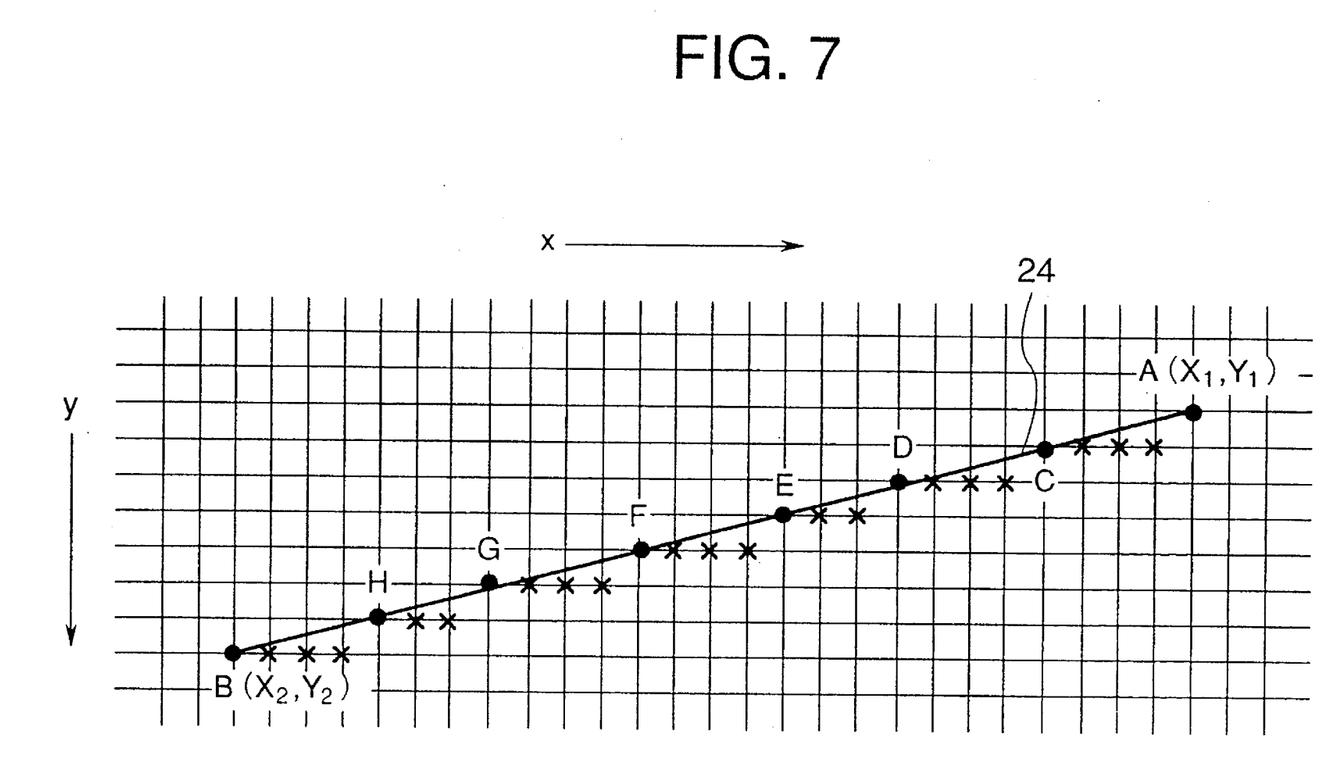
FIG. 7 is an Illustration which shows the relationship between picture elements of an ultrasound image and the data sampling line which coincides with such picture elements, according to the embodiment of the present invention.

As shown in FIG. 6, in the case where points A and B are designated for a B-mode image, the X and Y coordinates of the points A and B are determined by the read-out circuit 4. Once the X and Y coordinates have been obtained, a straight line which is passed through the points A ($X_1$, $Y_1$) and B ($X_2$, $Y_2$) can be determined by the following equation:

$$x = \frac{X_1 - X_2}{Y_1 - Y_2} \times y - \frac{X_1 Y_2 - X_2 Y_1}{Y_1 - Y_2}$$

using this formula, it is possible to determine a single value of "x" for every value of "y" along the line segment lying between the points A and B. Here, "y" is the number of sweep lines and both values "x" and "y" are an integer. Further, the figures after the decimal point of the value "x" are rounded. As a result, as illustrated in FIG. 7, each picture element shown by the points C, D, E, F, G, H coincide with or substantially coincide with the data sampling line 24.

From the ultrasound image data stored in the frame memory 2, the read-out circuit 4 selectively reads out, frame by frame, the ultrasound image data corresponding to each of the picture elements A, C, D, E, F, G, H, B, and then this data is displayed with the lapse of time on the monitor 18 via the M-mode frame memory 6 and the combining circuit 16.

However, because ultrasound image data exists within the frame memory 2 only at addresses that correspond to points of intersection (picture elements) of the matrix shown in FIG. 7, the slope of the straight line causes there to be few picture elements which coincide with the data sampling line 24 depending on its degree of inclination. Thus, the ultrasound image data that can be read out becomes extremely small, and this makes it impossible to obtain sufficient resolution when the living body is being observed.

Accordingly, it is at times necessary for the read-out circuit 4 to carry out a certain degree of interpolation for portions having picture elements that do not coincide with the data sampling line 24. The ways in which such interpolation can be carried out are explained below with reference to FIGS. 8(A), 8(B), 8(C) and 8(D).

As shown in FIG. 8, in the case where picture elements A, C, and E coincide with the data sampling line 24, the portions of the data sampling line 24 that lie within the spaces AC and CE do not coincide with the locations of picture elements.

Figure 8A:
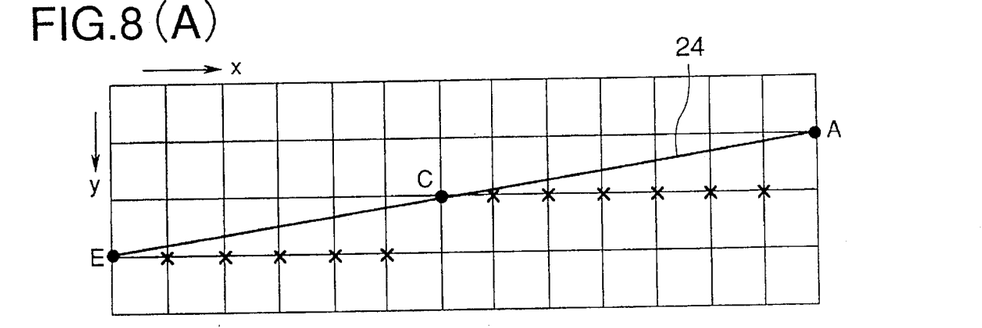
FIGS. 8(A), 8(B), 8(C) and 8(D) are drawings, each of which illustrates the way for correcting the dislocation between ultrasound image data which corresponds to the data sampling line and the positions of picture elements in the frame memory, respectively.

Therefore, as shown in FIG. 8(A), one way of interpolation is to first determine the Y values of the adjacent two picture elements that lie above and below the data sampling line 24 in each Y coordinate existing within each noncoinciding portion AC and CE, and then assume that the ultrasound image data corresponding to each picture element x that has the lesser value between the two Y values would be ultrasound image data corresponding to the data sampling line 24. Such data is then selectively read out in the same manner as described above.

Figure 8B:
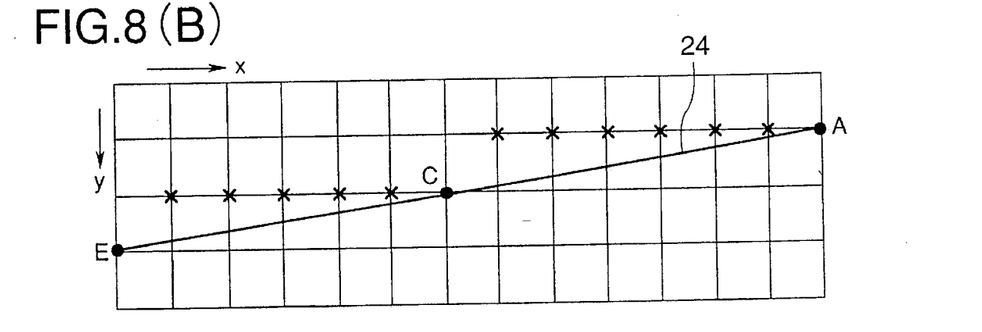

Another way of interpolation, as shown in FIG. 8(B), is to first determine the Y values of the adjacent two picture elements that lie above and below the data sampling line 24 in each Y coordinate existing within each noncoinciding portion AC and CE, and then assume that the ultrasound image data corresponding to each picture element x that has the greater value between the two Y values would be ultrasound image data corresponding to the data sampling line 24. Such data is then selectively read out in the same manner as described above.

Figure 8C:
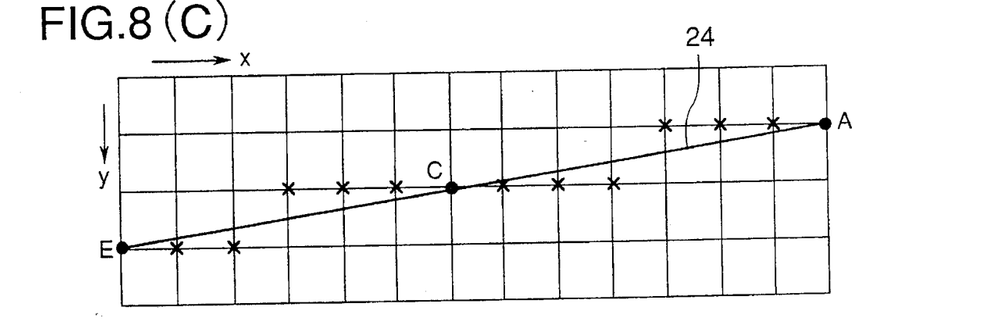

Yet another way of interpolation, as shown in FIG. 8(C), is to first determine the Y values of the adjacent two picture elements that lie above and below the data sampling line 24 in each Y coordinate existing within each noncoinciding portion AC and CE, and then assume that roughly half of each noncoinciding portion AC and CE has the lesser value between the two Y values and that the other half of each noncoinciding portion AC and CE has the greater value between the two Y values. The picture elements x having these assumed Y values are considered to be ultrasound image data corresponding to the data sampling line 24. Such data is then selectively read out in the same manner as described above.

As there is a high possibility that the ultrasound image has the same brightness value between adjacent picture elements, it is possible to display a high-resolution M-mode image without the need for a special calculating circuit if either of the interpolations described with reference to FIGS. 8(A), 8(B) and 8(C) is performed.

Figure 8D:
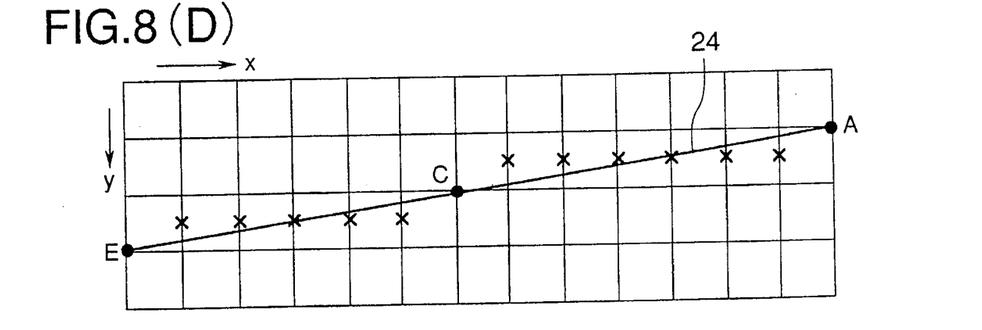

And yet another way of interpolation, as shown in FIG. 8(D), is to first determine the Y values of the adjacent two picture elements that lie above and below the data sampling line 24 in each Y coordinate existing within each noncoinciding portion AC and CE, and then obtain the average value of the two Y values of the picture elements in each noncoinciding portion. The thus-obtained average value indicated by x is then assumed to be ultrasound image data corresponding to the data sampling line 24 in each noncoinciding portion. Such data is then selectively read out in the same manner as described above. According to this way, it becomes possible to display more accurate M-mode images.

Therefore, even when there is no ultrasound image data that directly corresponds to the data sampling line 24, it is possible to obtain high resolution M-mode images by carrying out data interpolation as described above. In this regard, it should be noted that these interpolations are carried out through an interpolating circuit 5 shown in FIG. 2.

As described above, it is possible to obtain high resolution M-mode images by carrying out the either of the above interpolations as described. However, if the following process is carried out in addition to such interpolation, even higher resolution M-mode images can be obtained.

Figure 9:
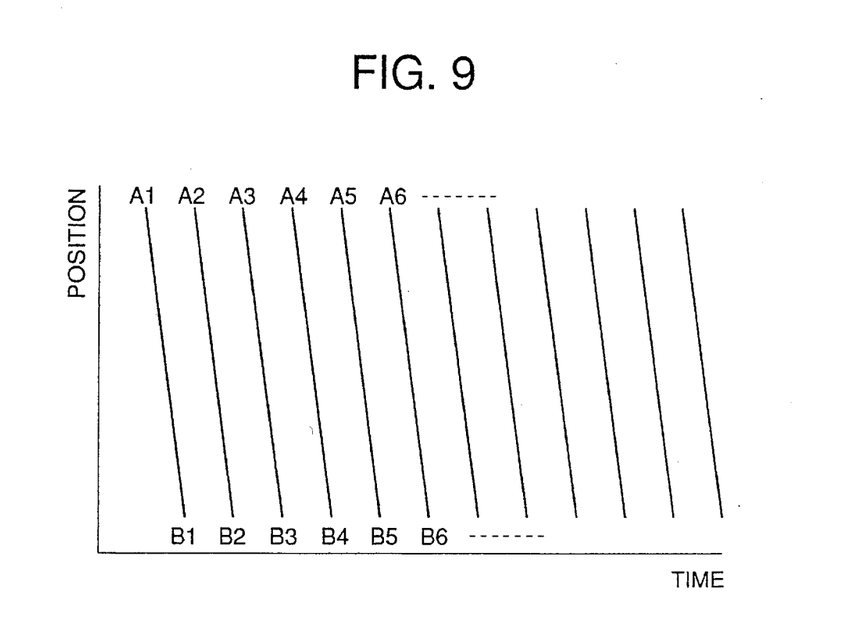
FIG. 9 is an illustration for explaining the phase correction for the M-mode image data obtained according to the present invention.

Namely, in the example shown in FIG. 3, a single line of M-mode data between points A and B was obtained from the single B-mode image data by the technique described above. However, the data at point A and the data at point B are not in the same phase. Namely, the data is collected at a frame rate of 20–60 frames/second. Therefore, for example, at a frame rate of 30 frames/second, there is a time difference of roughly 1/30 second between the time data that is collected at point A and the time data that is collected at point B. Accordingly, since such time delay affects the M-mode image displayed on the monitor it is necessary to carry out a phase correction like that shown in FIG. 9 in order to compensate this time delay.

Figure 10:
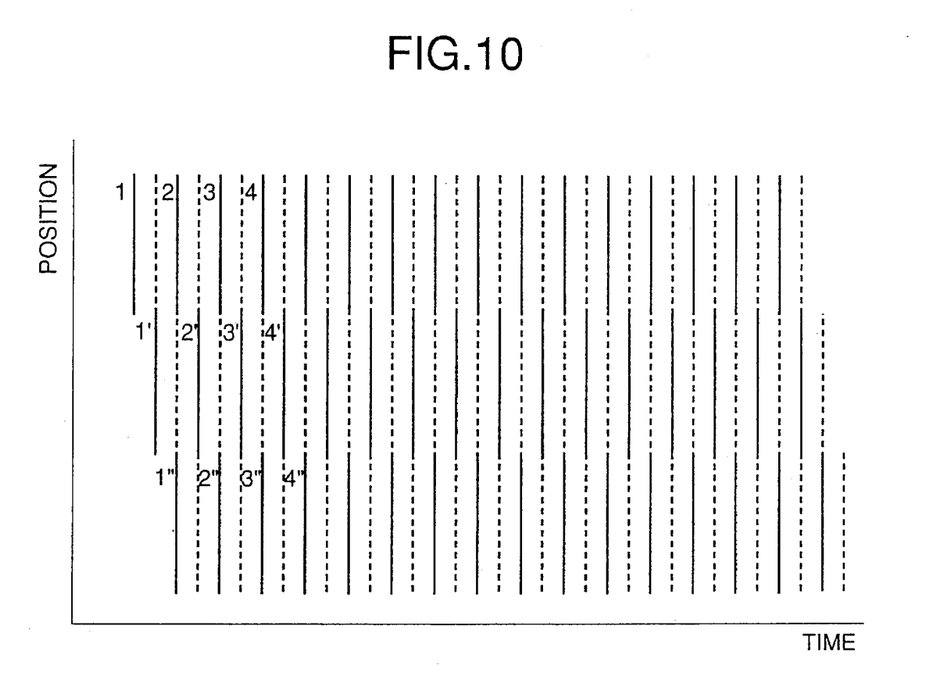
FIG. 10 is an illustration which shows the phase correction according to the present invention.

In the present embodiment, the phase correction is made by dividing the M-mode data which follows the slope of the designated data sampling line 24 into a plurality of portions. Preferably, the M-mode data is divided into three portions 1, 1' and 1" as shown in FIG. 10. Furthermore, interpolation is carried out for the dotted line portion of each line by using the actual data of the solid line portions positioned at the both sides thereof. In more details, for example, in the case of the third line, it includes one actual data portion indicated by the solid line portion 2, a dotted line portion and another actual data portion indicated by the solid line portion 1". and with regard to the dotted line portion an interpolation is made by using the data of two actual data portions positioned at the both sides thereof, that is the solid line portion 1' and the solid line portion 2'. In this way, the phase correction is carried out, thus enabling to obtain higher resolution M-mode images.

Furthermore, in the present embodiment, the M-mode display is carried out by selective reading out ultrasound image data which corresponds to the data sampling line 24 from the B-mode image data. However, such M-mode display can be made in association with a Doppler-mode display which shows the speed of motion of the portion of the living body being observed. Namely, according to the present invention, it is possible to freely establish a data sampling line for a two-dimensional Doppler image and then selectively read out only Doppler image data that corresponds to the data sampling line from the two-dimensional Doppler image data. Then, in the same manner as was described above for the display of M-mode data, such Doppler-mode image data which corresponds to the data sampling line is displayed in association with the lapse of time. In such a Doppler-mode display, the obtained Doppler-mode image data has dependency upon the forward direction of the ultrasound beams. Therefore, if the desired data sampling line can be established irrespective of the forward direction of the ultrasound beams and then a Doppler-mode image that corresponds to the data sampling line can be displayed, it is possible to accurately observe and diagnose the speed of motion, namely the state of motion, of the portion being observed.

Moreover, use of the diagnostic ultrasound apparatus according to the present embodiment is not limited to real time ultrasound diagnosis. It is also possible to carry out ultrasound diagnosis based on the image data which was already recorded on an image recording means such as a VTR or the like. In this case, a data sampling line is established for ultrasound images that are reproduced from the recorded ultrasound image and then ultrasound image data corresponding to the data sampling line is displayed with the lapse of time for the purpose of observation and diagnosis. This feature is especially helpful for situations where diagnosis time is limited, such as during group examinations.

As explained above, by using the diagnostic ultrasound apparatus according to the above embodiment of the present invention, it is possible to obtain an M-mode image for a desired position in a B-mode image irrespective of the forward direction of the ultrasound beams which forms the B-mode image. As a result, it enables observation of a specific portion of a living body to be carried out along any desired direction or course, thereby improving the ease and reliability of carrying out diagnosis, while at the same time making it possible to shorten the time it takes to perform such diagnosis.

Moreover, because scanning is carried out only within a specified ultrasound scanning range determined based on the designated data sampling line, the ultrasound image data for the data sampling line can be displayed with an improved frame rate, and this makes it possible to carry out accurate observation and diagnosis of even rapidly moving portions of a living body.

Finally, it should be understood that the present invention is not limited to the embodiments as described above. The scope and spirit of the invention will be decided only by the following claims.

What is claimed is:

1. A diagnostic ultrasound apparatus, comprising:

an ultrasound probe for transmitting and receiving ultrasound beams to and from an object to be observed;

a frame memory for storing two-dimensional ultrasound image data of the object obtained from said ultrasound beams received by said ultrasound probe;

a monitor for displaying at least a two-dimensional ultrasound image of the object formed on the basis of said two-dimensional ultrasound data stored in said frame memory;

means for freely setting desired course and range of at least one data sampling line for said two-dimensional ultrasound image displayed on said monitor, said data sampling line being set so as to pass at least two selected points irrespective of the forward direction of said ultrasound beams which form said two-dimensional ultrasound image;

read-out means for selectively reading out, from said ultrasound image data stored in said frame memory, ultrasound image data corresponding to said at least one data sampling line; and means for displaying an ultrasound image corresponding to said data sampling line on said monitor on the basis of said ultrasound image data which has been read out by said read-out means.

2. The diagnostic ultrasound apparatus as claimed in claim 1, further comprising scanning control means for setting a scanning range within said two-dimensional ultrasound image on the basis of said data sampling line and for controlling said probe so as to perform scanning only within said scanning range.

3. The diagnostic ultrasound apparatus as claimed in claim 2, wherein in said scanning control means said sampling line is represented by X and Y coordinates on the two-dimensional ultrasound image and said scanning range is determined on the basis of the largest and smallest X and Y values of said data sampling line on the X and Y coordinates.

4. The diagnostic ultrasound apparatus as claimed in claim 3, wherein said scanning range is defined by the scanning angle determined by the largest and smallest X and Y values of said data sampling line on the X and Y coordinates.

5. The diagnostic ultrasound apparatus as claimed in claim 4, wherein said scanning range is further defined by the depth of the scanning determined by the largest and smallest X and Y values of said data sampling line on the X and Y coordinates.

6. The diagnostic ultrasound apparatus as claimed in claim 1, wherein said frame memory has a plurality of picture elements arranged in matrix, and said diagnostic ultrasound apparatus further comprising means for interpolating the ultrasound data of said data sampling line which deviate from the locations of the picture elements.

7. A diagnostic ultrasound apparatus, comprising:

an ultrasound probe for transmitting and receiving ultrasound beams to and from an object to be observed;

a frame memory having a plurality of picture elements arranged in matrix for storing two-dimensional ultrasound image data of the object obtained from said ultrasound beams received by said ultrasound probe;

a monitor for displaying at least a two-dimensional ultrasound image of the object formed on the basis of said two-dimensional ultrasound data stored in said frame memory;

means for freely setting desired course and range of at least one data sampling line for said two-dimensional ultrasound image displayed on said monitor, said data sampling line being set irrespective of the forward direction of said ultrasound beams which form said two-dimensional ultrasound image;

read-out means for selectively reading out, from said ultrasound image data stored in said frame memory, ultrasound image data corresponding to said at least one data sampling line;

means for displaying an ultrasound image corresponding to said sampling line on said monitor on the basis of said ultrasound image data which has been read out by said read-out means;

means for interpolating the ultrasound data of said data sampling line which deviate from the locations of the picture elements; and means for performing phase correction for the delay time caused by the difference between data collecting times at the opposite ends of said data sampling line when the ultrasound image data corresponding to said data sampling line is displayed.

8. A diagnostic ultrasound apparatus, comprising:

means for transmitting and receiving ultrasound beams to and from a patient;

means for displaying a two-dimensional ultrasound image based on the received ultrasound beams;

means for freely setting a desired course for said displayed two-dimensional ultrasound image, said desired course passing at least two selected points irrespective of the forward direction of said ultrasound beams which form said two-dimensional ultrasound image;

means for sampling ultrasound data of said course; and means for displaying said sampled ultrasound data which shows changes in a region of the patient along the course with the lapse of time.

9. A diagnostic ultrasound apparatus, comprising:

a probe for transmitting and receiving ultrasound beams to and from an object to be observed;

memory means for storing B-mode image data of the object which is obtained from the ultrasound beams received by said probe;

a monitor for displaying a B-mode image on the basis of said B-mode image data; and means for obtaining M-mode image data along a desired data sampling line freely set on said B-mode image so as to pass at least two selected points irrespective of the forward direction of the ultrasound beams which form the B-mode image, said obtained M-mode image data forming an M-mode image to be displayed on said monitor.

10. A method of obtaining an M-mode image along any desired direction and range in a B-mode image displayed in a monitor, comprising the steps of:

transmitting and receiving ultrasound beams to and from an object to be observed to obtain B-mode ultrasound image data which can produce the B-mode image;

storing said B-mode ultrasound image data in a frame memory;

displaying the B-mode image based on the B-mode ultrasound image data on the monitor;

designating any desired course of a data sampling line in the B-mode image displayed in the monitor irrespective of the forward direction of the ultrasound beams which form the B-mode image; and producing an M-mode image of the object along said desired data sampling line on the monitor on the basis of ultrasound image data corresponding to said data sampling line which is selectively read out from said B-mode ultrasound image data stored in said frame memory.

11. The method as claimed in claim 10, further comprising the step of setting a scanning range within said B-mode image on the basis of said data sampling line and controlling the transmission and reception of the ultrasound beams so as to be performed only within said scanning range.

12. A method of diagnosing a cardiac function of a heart of a patient, comprising the steps of:

displaying on a monitor a B-mode image in which a tomographic image of a left ventricle of a heart of the patient appears;

designating any desired two points on said B-mode image in such a manner that a data sampling line formed between the two points passes through the left ventricle, the data sampling line being set irrespective of the ultrasound beams forming the B-mode image;

acquiring ultrasound image data along the data sampling line from ultrasound image data which forms the B-mode image; and displaying changes of the ultrasound image data along the data sampling line with the lapse of time on said monitor together with the B-mode image.

13. The method as claimed in claim 12, wherein the image of the left ventricle includes an image of a mitral valve and said data sampling line is set so as to pass through the mitral valve substantially perpendicular thereto.

* * * * *